(12) United States Patent
Soberon et al.

(10) Patent No.: US 8,945,467 B2
(45) Date of Patent: Feb. 3, 2015

(54) METHOD AND APPARATUS FOR THE STERILISATION OF ARTICLES

(75) Inventors: Felipe Soberon, Dublin (IE); Shane Glynn, Castlejordan Tullamore (IE); Paul Maguire, Dublin (IE); Stephen Daniels, Dublin (IE)

(73) Assignee: Arann Healthcare Ltd., Dublin (IE)

( * ) Notice: Subject to any disclaimer, the term of this patent is extended or adjusted under 35 U.S.C. 154(b) by 76 days.

(21) Appl. No.: 13/700,080

(22) PCT Filed: Feb. 17, 2011

(86) PCT No.: PCT/EP2011/052374
§ 371 (c)(1),
(2), (4) Date: Feb. 11, 2013

(87) PCT Pub. No.: WO2011/147595
PCT Pub. Date: Dec. 1, 2011

(65) Prior Publication Data
US 2013/0136655 A1     May 30, 2013

(30) Foreign Application Priority Data
May 27, 2010   (IE) .................. S2010/0346

(51) Int. Cl.
| A61L 2/00 | (2006.01) |
| A61L 9/00 | (2006.01) |
| A62B 7/08 | (2006.01) |
| A61L 2/20 | (2006.01) |
| A61L 2/26 | (2006.01) |
| A61L 2/14 | (2006.01) |

(52) U.S. Cl.
CPC ... *A61L 2/20* (2013.01); *A61L 2/26* (2013.01); *A61L 2/14* (2013.01); *A61L 2/202* (2013.01); *A61L 2/208* (2013.01); *A61L 2202/122* (2013.01); *Y10S 422/906* (2013.01)
USPC .............. 422/22; 422/28; 422/32; 422/121; 422/306; 422/906

(58) Field of Classification Search
CPC ............ A61L 2/00; A61L 12/00; A61L 2/035
USPC ............... 422/22, 28, 32, 121, 186, 292, 306, 422/906–907
See application file for complete search history.

(56) References Cited

U.S. PATENT DOCUMENTS

2004/0161361 A1 * 8/2004 Uhm et al. .................. 422/30
2006/0156983 A1   7/2006 Penelon et al.

FOREIGN PATENT DOCUMENTS

| CN | 201242995 | 5/2009 | |
| JP | 2006263245 | * 10/2006 | ............... A61J 1/10 |
| JP | 2006296848 | 11/2006 | |
| KR | 20030060644 | 7/2003 | |

OTHER PUBLICATIONS

International Search Report on related PCT application (PCT/EP2011/052374); International Searching Authority (EPO) dated May 11, 2011.

* cited by examiner

*Primary Examiner* — Monzer R Chorbaji
(74) *Attorney, Agent, or Firm* — Klein, O'Neill & Singh, LLP (57) ABSTRACT

A method and apparatus for sterilizing an article. The method comprises placing an article in a sterilization container, generating oxidizing plasma radicals at atmospheric pressure, and providing the oxidizing plasma radicals to the sterilization container to sterilize the article in the container.

19 Claims, 5 Drawing Sheets

METHOD AND APPARATUS FOR THE STERILISATION OF ARTICLES

CROSS-REFERENCE TO RELATED APPLICATION

This application is a national phase filing, under 35 U.S.C. §371(c), of International Application No. PCT/EP2011/052374, filed Feb. 17, 2011, the disclosure of which is incorporated herein by reference in its entirety.

FEDERALLY SPONSORED RESEARCH OR DEVELOPMENT

Not Applicable

FIELD OF INVENTION

The present invention relates to the sterilisation of articles. In particular, the invention relates to those articles which can not be sterilised through the use of high temperatures, due to the fact that the high temperatures would cause damage and render them useless, such as sterilisation by means of an autoclave for example. In addition, the invention relates to those articles which are not suitable for sterilisation through the use of a vacuum chamber.

BACKGROUND OF THE INVENTION

The sterilisation of articles is of great concern today, in order to reduce the spread of disease throughout the world. One environment where sterilisation is of major importance is the medical environment, in order to reduce the risk of infection transmission between patients and/or staff.

The supply of sterile equipment in hospitals is usually under the responsibility of the Central Sterile Supply Department (CSSD). This department receives the medical and surgical instruments and supplies for cleaning and sterilisation. Typically the process involves automated washers followed by autoclaving at a temperature of 121° C. or above. It will be appreciated however that due to the heat present in an autoclave, some articles are not suitable for the autoclave procedure, such as for example endoscopes.

An alternative to the autoclave is a hydrogen peroxide vapour and plasma sterilizer system, such as the one developed by Johnson & Johnson Medical Inc., and described in U.S. Pat. No. 5,876,666. Other systems using hydrogen peroxide vapour as a precursor to plasma treatment for sterilisation purposes are described in U.S. Pat. No. 4,643,876 and No. 4,756,882, both of which are patents in the name of Surgikos Inc.

U.S. Pat. No. 5,084,239 in the name of Abtox Inc. describes a process of, first, exposing a medical instrument to a antimicrobial agent such as hydrogen peroxide and/or peracids and, second, exposing the instrument to a low pressure plasma discharge with gases such as argon, oxygen, helium, nitrogen, hydrogen or a mixture of same.

The Johnson & Johnson system described in U.S. Pat. No. 5,876,666 has been commercialized by ASP (Advanced Sterilization Products) as the STERRAD system [Validation of a low-temperature, low pressure, vaporized aqueous hydrogen peroxide-based, plasma sterilisation system—STERRAD 100S sterilizer, EFHSS Conference 2004, Izmir/Cesme, Turkey]. This system operates at pressures below one atmosphere. It operates by exposing medical instruments placed in a vacuum chamber to hydrogen peroxide vapour and then it runs low temperature plasma. The vapour exposure and the plasma process are run in sequence taking approximately 30 minutes for each step. This hydrogen peroxide—plasma sequence is typically run 2 to 3 times per load. The sterilisation cycle is then validated by cultivating a series of biological indicators for 24 to 72 hours, with the biological indicators containing spores of *Geobacillus stearothermophilus* ATCC 7953 (American Type Culture Collection). Multiple biological indicators are processed during the sterilisation of the load and are cultivated together with unprocessed indicators after the sterilisation cycle. It will be appreciated that processed indicators should not develop a bacterial population in order to validate the sterilisation cycle.

Another plasma sterilizer apparatus is described in International patent publication NO. WO 03/090796 by Human Meditek Co. Ltd. Similar to the STERRAD system, this system also uses hydrogen peroxide vapour, but is distinguished from the STERRAD process by the fact that the plasma discharge is generated remotely. This allows the plasma byproduct radicals to fill the treatment chamber, while at the same time not exposing the medical instruments directly to the plasma.

Another apparatus with a remote plasma chamber connected to a sterilizing chamber is described in Abtox Inc.'s U.S. Pat. No. 5,413,758. Again, the medical instruments in this apparatus are exposed to the plasma by product radicals. International patent publication No. WO 2009/078361 of Saga University and University of the Ryukyus meanwhile describes an oxygen sterilizer, with an upstream ICP plasma source generating a high density of radicals downstream for sterilisation.

Another low pressure sterilizer, STERIZONE®, was developed by TSO3 Inc., and is described in their U.S. Pat. No. 7,128,872. It uses a mixture of water vapour and ozone at low pressure inside a chamber to perform the sterilisation. The process is divided into four main steps: vacuum (1 Torr), humidification, injection (of ozone) and exposure (to ozone and water vapour). The system is pre-conditioned by heating the chamber to prevent water vapour condensation, by setting the system temperature above water boiling point for the working pressure. The mix of the water vapour and ozone form hydroxyl radicals, these perform the sterilisation through their oxidizing action. The cycle takes about four and a half hours. Similar to the STERRAD® system, this system uses biological indicators to validate the performance of the sterilisation.

Although the above plasma sterilizing systems are suitable to non-autoclavable medical instruments, they are limited as to what articles they can sterilise. This is due to the fact that they are operated in a low pressure environment.

One alternative to low pressure sterilizing systems is described in US Patent No. 2004/0022673. This system operates a sterilisation chamber at atmospheric pressure. It includes four process stages, namely: (1) the introduction of oxidising agent chemicals such as peracetic acid, (2) the application of high energy gas plasma field, (3) the application of further plasma in combination with agent/biocides such as hydrogen peroxide, chlorine/hypochlorate, iodine and other aldehydes and, (4) the purging of the sterilisation chamber. The total sterilisation processing time of this system can be up to two hours. However, some of the drawbacks of this system include the use of toxic gases, which may not be suitable for use with some articles, as well as the limitation as to what articles can be sterilised, due to the fact that the sterilisation chamber is a fixed volume chamber.

A second alternative to low pressure sterilizing systems is described in US Patent No. 220/0037736. This system sterilizes an article by means of a plasma, and in the presence of moisture at a relative humidity of more than 50% using non-biocidal gas containing oxygen and nitrogen, such as for example air. The article is placed inside a sealed enclosure inside which a plasma discharge is sustained, where said discharge is not in contact with the article. The system includes three process stages, namely: (1) the introduction of humidified non-biocidal gas and first plasma discharge, (2) a second plasma discharge sustained by a second plasma source, or alternatively run with different parameters than the previous plasma discharge and, (3) rinsing with a non-humidified gas. A drawback to this system is however the use of humidified oxygen/nitrogen gas, which can lead to the formation of nitric acid on the article, which is a toxic and corrosive compound.

A third alternative to low pressure sterilizing systems is described in US Patent No. 2004/0161361. This system generates an oxygen plasma discharge inside a non-oxidizing metallic chamber, effectively generating ozone. In other embodiments of the system, oxygen gas may be mixed with moisture and/or hydrogen peroxide, or indeed run with air. The use of oxygen is recommended due to the formation of nitric acid, when operating the system with humidified air, which may have harmful effects on human body. Some disadvantages to this system include the requirement to use oxygen gas, and the limitation to those articles which can be sterilised in a fixed volume metallic chamber.

Although the above plasma sterilizing systems are operated at atmospheric pressures, their processes are complicated by the need to introduce, monitor and control chemicals and/or moisture. Other disadvantages of these described systems include the use of consumables, such as chemicals and/or gases, and the fact that hazardous compounds can form on the articles, such as nitric acid.

Furthermore, in hospitals, even after effective sterilisation of most medical instruments, it will be appreciated that there are still a series of articles and places where infectious diseases may be transmitted. Studies suggest that bacteria can be transmitted via contact with contaminated surfaces and by inhaling contaminated particles (airborne). Some of the highest profile bacteria are antibiotic resistant bacteria found in hospitals. These include some bacteria, known as super-bugs, such as Meticillin-Resistant *Staphylococcus aureus* (MRSA), *Clostridium difficile* (*C. diff*) and Vancomycin-resistant enterococci (VRE). These are some of the most common Health Care Associated Infection (HCAI) diseases, i.e. of an infection that is acquired as a result of contact with the healthcare system.

An environmental study at Beaumont Hospital in Dublin in Ireland found more than half of surface samples tested positive for MRSA in isolation rooms, while 28% of air samples were also found positive for MRSA [T. Sexton et al., J. Hosp. Infect. 62, 187 (2006)]. In this study it was also found that more than half of the beds and mattresses sampled were positive for MRSA. The potential risk of infection transmission through bed mattresses and pillows was also highlighted [E. Creamer and H. Humphreys, J. Hosp. Infection, 69, 8 (2008)]. A lack of an effective and practical solution for sterilisation of beds in general was also noted. It will be appreciated therefore that hospital and nursing home beds are some of the places where bacteria colonies may build up in large quantities.

To prevent patient to patient transmission, beds have to be cleaned, disinfected and sterilised. The sterilisation method has to be able to kill all types of bacteria and viruses. In particular, the removal of spores is of great importance, being reproductive structures adapted for dispersal and survival for extended periods of time in unfavourable conditions. It is found that bacteria resistance to bactericidals is significantly higher in spore state than in the vegetative state.

Another potential target for plasma sterilisation is prions. Prions are infectious agents composed primarily of protein. All known prion diseases affect the structure of the brain or other neural tissue, and all are currently untreatable and fatal. An example of prion disease in humans is Creutzfeldt-Jakob disease (CJD), the human variation of the bovine disease known as "mad cow disease". Prion diseases are resistant to ultraviolet radiation and heat. Sterilizing prions involves the denaturation of the protein, a process by which proteins or nucleic acids lose their tertiary structure and secondary structure by the application of some external stress or compound.

It will be appreciated therefore that there exists a need to provide a sterilisation method and apparatus suitable for use with all shapes and sizes of articles and which can be used in most environments.

SUMMARY OF THE INVENTION

The present invention provides a method for sterilising an article comprising:
placing an article in a sterilisation container;
generating oxidizing plasma radicals at atmospheric pressure; and
providing the oxidizing plasma radicals to the sterilisation container to sterilise the article in the container.

By enabling the article to be sterilised at atmospheric pressure, the method can be used on all types of articles and is suitable for use in most environments.

Preferably, the step of generating oxidizing plasma radicals at atmospheric pressure may comprise the steps of:
applying a high voltage to an atmospheric plasma cell so as to generate a plasma; and
providing a flow of gas through the plasma to generate the oxidizing plasma radicals.

The method may further comprise the step of:
filtering the plasma radicals from the gas and releasing the filtered gas from the sterilisation container to the atmosphere.

The method may further comprise the step of releasing the filtered gas to the atmosphere only once the sterilisation container has reached a predetermined pressure level.

The method may further comprise the steps of:
powering off the high voltage to the atmospheric plasma cell once the article is sterilised; and
removing the sterilised article from the sterilisation container once the plasma radicals have been filtered from the sterilisation container.

The method may further comprise the step of providing a gas to the sterilisation container prior to the removal of the sterilised article.

The gas may be an inert gas.

Preferably, the gas comprises dry air with a humidity level below 50%.

The present invention also provides an apparatus for sterilising an article, the apparatus comprising:
a sterilisation container for receiving an article to be sterilised;
a plasma radical generator for generating oxidizing plasma radicals at atmospheric pressure; and
means for providing the oxidizing plasma radicals to the sterilisation container.

The plasma radical generator may comprise:
a high voltage power supply coupled to an atmospheric plasma cell for generating a plasma discharge; and
a gas source for providing a flow of gas to the atmospheric plasma cell.

The apparatus may further comprise an exhaust system coupled to the sterilisation container for filtering the plasma radicals from the gas prior to releasing the gas from the sterilisation container to the atmosphere.

The exhaust system may comprise at least one filtering means.

The at least one filtering means may comprise a catalytic converter.

The catalytic converter may comprise a baffle cylinder incorporating steel wool.

Alternatively, the catalytic converter may comprise an ozone destruction catalyst.

The apparatus may further comprise means for releasing the filtered gas to the atmosphere only once the sterilisation container has reached a predetermined pressure level.

The means for releasing the filtered gas to the atmosphere only once the sterilisation container has reached a predetermined pressure level may comprise a back pressure valve provided on the gas outlet of the sterilisation container.

In one embodiment of the invention, the atmospheric plasma cell is separate to the sterilisation container and the means for providing the oxidizing plasma radicals to the sterilisation container comprises a gas inlet port located on the sterilisation container for connecting the atmospheric plasma cell to the sterilisation container.

The apparatus may further comprise a means for providing an even distribution of oxidizing plasma radicals within the sterilising container.

The means for providing an even distribution of the oxidizing plasma radicals may comprise a plurality of pipes coupled to the gas inlet port of the sterilisation container, each pipe having a plurality of apertures distributed along their length.

Alternatively, the means for providing an even distribution of the oxidizing plasma radicals comprises a custom nozzle coupled to the gas inlet port.

The apparatus may further comprise a non return valve located adjacent to the gas inlet port, to prevent a back flow of oxidizing plasma radicals to the atmospheric plasma cell.

In another embodiment, the atmospheric plasma cell is located within the sterilisation container, and the means for providing the oxidizing plasma radicals to the sterilisation container comprises a circulation means located in the sterilisation container to circulate the plasma radicals.

Advantageously, the atmospheric plasma cell comprises a shielding tube, to prevent the electrical discharge from the plasma cell reaching the article to be sterilized.

The circulation means may comprise a fan.

The apparatus may further comprise a sealable opening means provided on the sterilisation container for receiving the article to be sterilised.

The opening means may comprise an airtight seal.

Preferably, the gas source comprises air.

Advantageously, the gas source is generated from an air compressor fitted with an air drying unit.

The sterilisation container may comprise a plastic bag.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE INVENTION

As is clear from the background to the invention section, plasma technology offers a simple and effective method to kill all types of bacteria and viruses. The present invention therefore uses plasma technology to kill bacteria and virus, but through a technique which generates plasma products, including oxidizing radicals, at atmospheric pressures at room temperature and exposes them to contaminated surfaces. This approach differs from the current state-of-the-art plasma sterilisation systems, which operate at low pressure (below atmosphere), thus limiting their applicability to articles that can fit in a vacuum chamber. In fact, the present invention is not limited to operation in any particular size of chamber. This is also in contrast to some of the current state-of-the-art systems described above, which, even though operated at atmospheric pressures, must use fixed volume chambers, due to their operation requirements, thus limiting their applicability to articles that can fit in such chambers. These systems also have the further drawback of requiring additional controls and sensors to monitor parameters such temperature, pressure, gas/chemicals/moisture injection and detection of harmful compounds. The system of the present invention also differs from those plasma sterilisation systems which operate at atmospheric pressure and which use a combination of consumables (e.g. gases/chemicals) and/or moisture, and as a result may damage the article, or harmful compounds may form on the article, as previously described.

By generating a combination of oxidizing radicals using only air, the plasma products attack the bacteria, removing its protective layers and breaking its DNA. The plasma radicals physically remove the bacteria from surfaces by eroding them away, and then kill them by destroying their genetic code. The plasma radicals constitute antimicrobial active species. These species include ozone, atomic oxygen, and free radicals, such as superoxide, hydroxyl and nitric oxygen [T. C. Montie et al., IEEE Trans. Plasma Sci., 28, 41 (2000)]. It should be noted that while ozone and hydroxyl are strong oxidizing agents present in the radical by-product mixture, they are not exclusive to the by-product mix.

In order to achieve maximum efficiency during the sterilisation process, the generated plasma radicals should be contained in a volume surrounding the article to be sterilised. This ensures a high concentration of radicals, resulting in an increase in the sterilisation action and a reduction of the sterilisation processing time.

Figure 1:
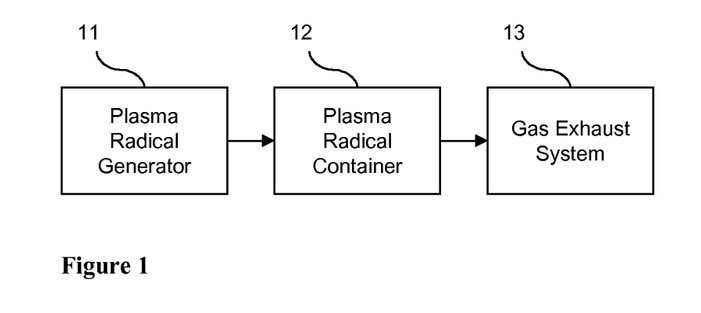
FIG. 1 is a block diagram of an embodiment of the main components of the present invention.

FIG. 1 shows a block diagram of an embodiment of the main components used to perform the present invention. A plasma radical generator 11 generates plasma radicals. The generated plasma radicals are then passed to a plasma radical container 12, where the sterilisation process takes place. The plasma radical container 12 may also be referred to as the sterilisation container. A gas exhaust system 13 is responsible for removing the radicals generated during the process.

Figure 2:
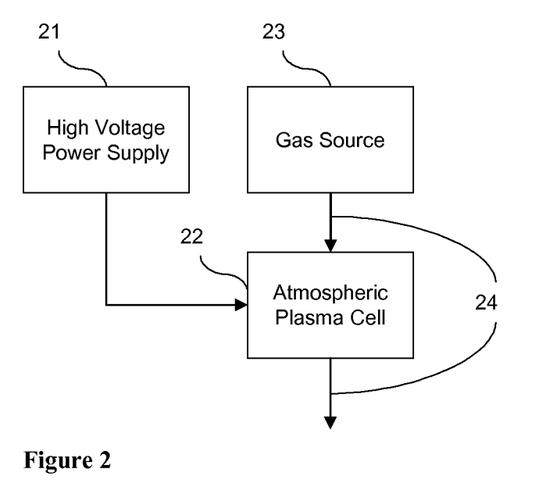
FIG. 2 is a block diagram of the components of the plasma radical generator.

FIG. 2 shows a block diagram of the components comprising the plasma radical generator 11, namely an atmospheric plasma cell 22, a high voltage power supply 21 and a gas source 23. The atmospheric plasma cell 22 is connected to the high voltage power supply 21 for generating the plasma. The gas source 23 is adapted to provide a continuous flow of gas into the atmospheric cell 22. This gas must be such that it will generate oxidizing plasma radicals. The gas source may take any suitable form, such as a gas bottle, a gas outlet pipe or an air gas compressor. In an embodiment of the present invention, the gas source is air from an oil free air compressor. In a preferred embodiment, the compressor is fitted with an air drying unit. The air compressor takes in normal room air and passes it through a drying unit. The resulting dry air is such that the humidity level is below 50%. By using dry air to generate the plasma radicals, it ensures the formation of nitric acids is below 2 parts per million (PPM). This corresponds to the safe limit provided by the National Institute for Occupational Safety and Health (NIOSH). Furthermore, no additional consumables are required, such as gas bottles. Ducts and fittings 24 feed the gas through the gas source 23 into the atmospheric plasma cell 22. The gas flow forces the gas through the plasma discharge in the plasma cell 22, generating the radicals. These are then fed or passed into the sterilisation container 12 through ducts and fittings. These oxidizing plasma radicals generated by the nitrogen/oxygen mixture in air being fed through the plasma have lifetimes in the order of thousands of seconds [I. A. Kossyi et al., Plasma Sources Sci. Technol., 1, 207 (1992)], thus ensuring a good supply of radicals into the sterilising container 12. The gas flow also prevents the formation of arcs inside the atmospheric cell 22, which could otherwise cause significant erosion of the electrodes of the plasma cell, and thus promotes plasma uniformity.

Figure 3:
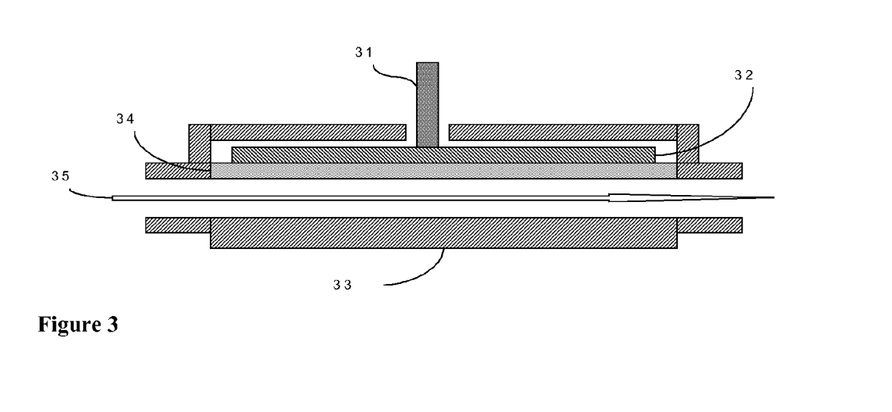
FIG. 3 is a cross-sectional view of the atmospheric plasma cell.

FIG. 3 shows a cross sectional view of the atmospheric plasma cell 22 of the plasma radical generator 11. The atmospheric cell 22 comprises two electrodes for generating the plasma, namely a high voltage electrode 32 and a ground electrode 33, with the high voltage being fed from the high voltage power supply 21 to the high voltage electrode 32 of the atmospheric plasma cell 22 through an electrical feedthrough 31. When in use, the gas 35 from the gas source 23 is fed through in between the electrodes in order to generate the oxidizing plasma radicals. A piece of insulating dielectric material 34 located on the surface of one of the electrodes prevents arcing between the electrodes.

In the preferred embodiment of the present invention, the high voltage power supply 21 generates high voltage in the range of kilo-Volts at frequencies between 1 and 500 kHz. However, it should be appreciated that in alternative embodiments radio frequency supplies in the range of MHz, such as 13.56 MHz, or microwave sources in the range of GHz, such as 2.45 GHz, could equally well be used.

It is important to note that in accordance with the present invention the cell 22 is not evacuated, and that therefore the plasma discharge is operated at atmospheric pressure. The exhaust system 13 comprises a series of gas filters and catalytic converters to remove the plasma radicals from the gas before releasing it back into the environment.

Figure 4:
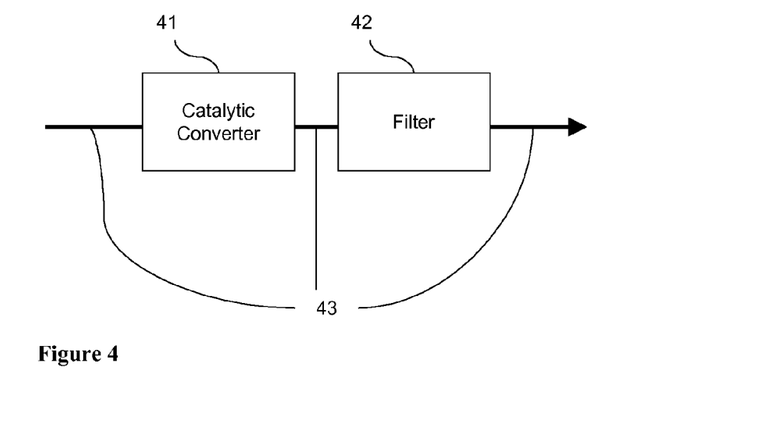
FIG. 4 is a block diagram of the components of the exhaust system.

FIG. 4 shows a block diagram of the components of the exhaust system 13. In one embodiment of the present invention, the radical filter comprises a catalytic converter 41 taking the shape of a baffle cylinder placed in line with the exhaust duct 43. For example, it can be placed at the outlet of the exhaust duct, or at any suitable location along the exhaust line 43. In one embodiment of the invention, the baffle cylinder is filled with ultra fine steel wool. The steel wool reacts with the oxidizing radicals, in particular with ozone, one of by-product radicals of highest concentration produced by atmospheric plasma discharges, so as to remove them from the exhaust gas through a catalytic conversion process. (The use of steel wool for the destruction of ozone is reported [W. C. Neely et al., J. Phys. E: Sci. Instrum., 8, 543 (1975)]). Alternatively, a commercial ozone destruction catalyst may be used, such as CARULITE® 200 or activated carbon. In one embodiment, an additional filter 42 can be used to remove particles ranging from sizes of a few microns in diameter. This additional filtering further prevents airborne microbe spread, as microbes may live on the surface of dust particles which are circulated by ventilation systems, which results in the spread of infections across indoor environments.

Figure 5:
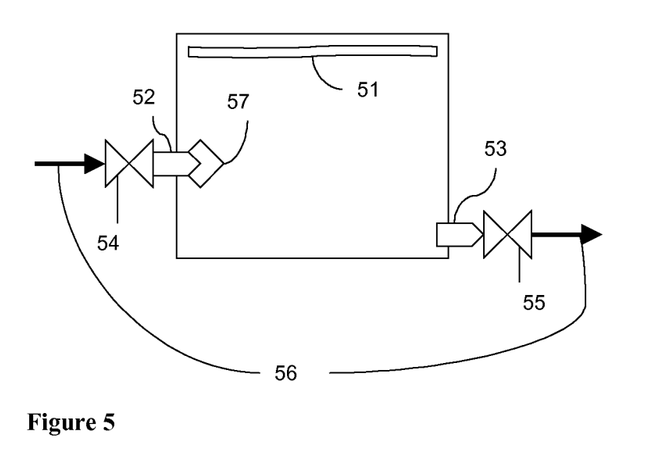
FIG. 5 shows the components of the sterilisation container.

In the described embodiment of the invention, the plasma radical container or sterilizing container 12 takes the form of a plastic bag. Any other suitable containing means could however equally be used in place of a plastic bag. In one embodiment, the plastic bag is made of high tensile heavy duty polyethylene.

FIG. 5 shows the components of the sterilisation container bag 12. The bag comprises a gas inlet port 52 for receiving the plasma radicals from the plasma radical generator 11, a gas outlet port 53 to exhaust the gas in the bag to the exhaust system 13 and an air tight seal 51. The air tight seal 51 is opened to place an article inside the bag 12 for sterilisation and closed to prevent the plasma radicals from exiting the bag 12. The in and out gas ports and ducts to which they are connected are designed so that a positive pressure may be built up inside the bag, inflating it to its maximum volume. In one embodiment this is achieved by using a back pressure valve 55 on the gas outlet port 53, to allow gas through only once it is above a certain bag pressure level. Additionally, a non-return valve 54 may be fitted at the gas inlet port 52, to prevent a back flow of radicals to the atmospheric plasma cell 22. These valves 54 and 55 also act to prevent gas release from the bag 12 when the in and out ducts 56 are disconnected from the bag inlet port 52 and outlet port 53. This allows sealed transport and storage of the articles within the bag 12.

Figure 6:
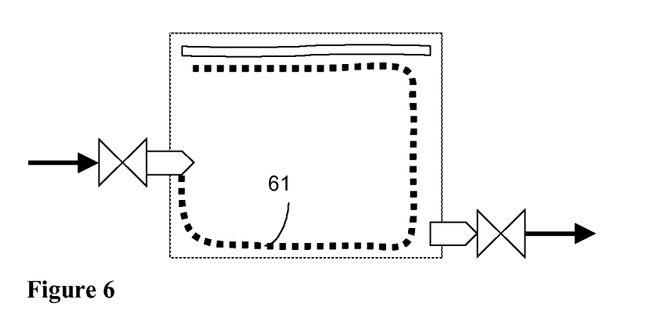
FIG. 6 shows the embodiment of the sterilisation container where a series of pipes are placed inside the sterilisation container.

The bag 12 is adapted so that gas flow and radical distribution inside the bag 12 maximises the sterilisation action evenly across the volume of the bag 12. This is achieved in one embodiment of the invention by providing a custom nozzle 57 design at the gas inlet port 52, to ensure uniform gas spread distribution. In an alternative embodiment, a series of thin pipes 61 having outlet gas holes distributed along the length of the pipes 61 can be placed inside the bag 12, by attachment to the inner walls of the bag 12, as is shown in FIG. 6. It will be appreciated that this internal pipe system emulates an irrigation system fed by the incoming plasma radical gas, and again ensures a uniform distribution of the radicals across the volume of the bag 12.

It will be appreciated that the type of plastic bag used should be tailored to the article to be sterilised. For example, if hospital bed mattresses and pillows are to be sterilised, the bag should be of a suitable size to accommodate these articles. This ensures that the bag volume is optimised to provide a local and effective sterilisation process. It should be noted also that given the oxidizing properties of the plasma radicals, the bag will have a usage lifetime limited to a certain number of hours of exposure to plasma radicals.

Figure 7:
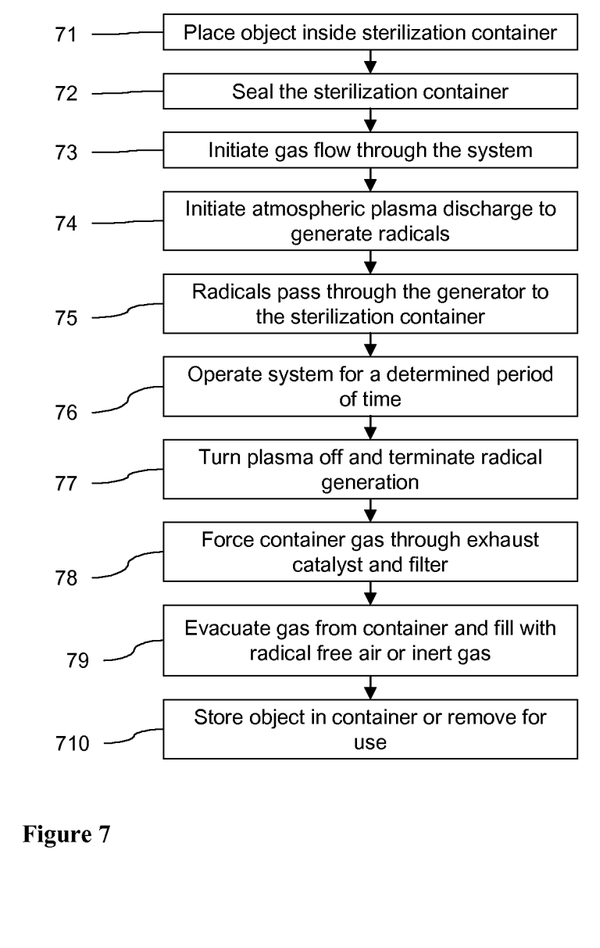
FIG. 7 shows the main steps in the process flow of the method of sterilisation of the present invention.

FIG. 7 details the main steps in the process flow of the method of sterilisation of the present invention. From a practical point of view it is preferred to place the article inside the sterilization container bag 12 before connecting it to the plasma radical generator 11 and the gas exhaust system 13. Therefore, in the preferred embodiment of the invention, one or more articles to be sterilised should first be placed inside the sterilizing container 12, namely the plastic bag (step 71). The bag is then zipped sealed closed to ensure it is air tight, to prevent the plasma radicals from exiting the bag (step 72). The bag should then be coupled to the plasma radical generator 11 by connecting the ducts 56 provided between the plasma radical generator 11 and the gas inlet 52. The bag should also be coupled to the gas exhaust system 13 by connecting the ducts 56 provided between the gas exhaust system 13 and the gas outlet port 53. The gas source 23 should then be turned on (step 73). This allows a constant flow of gas through the atmospheric plasma cell 22 and the bag 12. In accordance with the preferred embodiment of the invention, this gas comprises air with a humidity level of below 50%. Once the system achieves a desired gas flow, the high voltage supply 21 to the plasma cell 22 is turned on. This causes a high voltage between the electrodes 32 and 33, which strikes a plasma discharge inside the atmospheric plasma cell 22 (step 74). Oxidizing plasma radicals are then generated by the gas being fed through this plasma. These radicals pass through the radical generator 11 to the bag 12 in which the article is located, so as to sterilise the article (step 75). During the process, the gas is re-circulated or passed through the system and exhaust filters before being released to the environment.

The system is run for a certain period of time corresponding to the time necessary to perform the sterilisation of the article within the bag (step 76).

Once the plasma sterilisation cycle time is completed, the plasma is turned off to terminate the plasma radical generation, by turning off the high voltage power supply 21 to the plasma cell 22 (step 77). The gas inside the bag 12 is then forced through the radical destruction catalyst and filter comprising the exhaust system 13 before being exhausted to the atmosphere (step 78). The bag 12 may be filled up with radical free fresh air prior to opening the bag (step 79). This is achieved by first sucking the gas out of the bag 12 through the exhaust system 13 and then filling the bag 12 with radical free fresh air. Alternatively, radical free gas may be circulated for a period of time until the sterilization gas inside the bag 12 has been displaced out of the bag 12.

It will be appreciated that once the plasma is turned off there is no more radical generation by the atmospheric plasma cell 22. Hence the gas circulated through the plasma cell 22 is radical free gas. Furthermore, the same set of valves and ducts used to feed the radicals through the sterilisation container bag 12 are used to feed the radical free gas.

In step 710, the sterilised article is either removed from the bag 12, or alternatively stored in the bag 12 for future removal when required for use. If the article is to be stored in the bag 12, the bag 12 may be filled up with an inert gas such as nitrogen. The gas must first be sucked out of the bag 12 before filling the bag 12 with the required gas. Alternatively, the gas in the bag 12 may be sucked out, leaving little or no gas inside, with no gas fill afterwards. A valve on the bag 12 may let air inside the bag 12 when required prior to opening the bag 12 in this situation. This may be an additional valve on the bag 12, or one of the existing valves located on the inlet 52 or outlet 53 ports.

In the preferred embodiment of the invention, the bag 12 is disconnected from the radical generator 11 and the exhaust system 13 prior to the removal of the article/object from the bag 12 after completion of the sterilisation process. Similarly, if the article is to be kept inside the bag 12, it is preferred to disconnect the bag 12, so as to leave the plasma radical generator 11 and the exhaust system 13 available to be used with another bag 12.

It will be appreciated that the concentration of plasma radicals generated by the atmospheric plasma cell 22 depends on the high voltage power applied, the gas mixture and the gas flow. These parameters can be optimised to generate a sufficient concentration of plasma radicals for the sterilisation process of a particular article. For example, the higher the voltage applied, the higher the plasma densities, and therefore the higher the concentration of radicals which will be produced. It will further be appreciated that the time required to perform the sterilisation process is dependent on the radical concentration in the sterilisation container 12.

Figure 8:
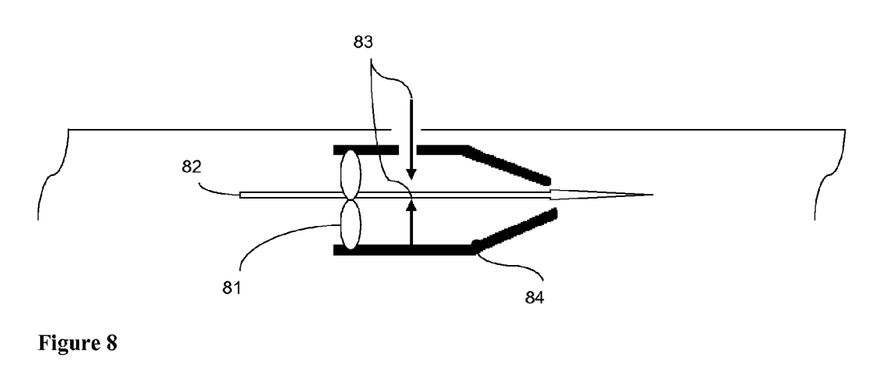
FIG. 8 shows a cross sectional view of the embodiment where the atmospheric plasma cell is located within the sterilisation container.

In an alternative embodiment of the sterilising system of the present invention, the atmospheric plasma cell 22 is placed within the bag 12, rather than connected to it. FIG. 8 shows a cross sectional view of this embodiment. This embodiment operates in accordance with the same principles as those previously described with regard to the previous embodiment. However, an air blower or fan 81 is also provided to circulate the gas 82 through the discharge and transport the radicals around the bag 12. Furthermore, the electrodes 83 are concealed within a shielding tube 84, to prevent the electrical discharge from reaching the article to be sterilized inside the bag 12. In one embodiment, the electrodes 83 are made of tungsten tips. It should be noted that these will be slowly eroded as the plasma discharge is run; limiting the number of hours the atmospheric plasma cell 22 may be used. This time can be designed to be matched to the maximum number of hours which the bag 12 may be exposed to the plasma radicals. In this way, the lifetime of the whole bag 12 is safely limited by its design, thus preventing over use that may result in radical leak to the atmosphere.

The invention claimed is:

1. A method for sterilizing an article comprising:
   placing an article in a sterilization container;
   generating oxidizing plasma radicals at atmospheric pressure;
   providing the oxidizing plasma radicals to the sterilization container to sterilize the article in the container; and
   evenly distributing the oxidizing plasma radicals within the sterilization container.

2. The method of claim 1, wherein the step of generating oxidizing plasma radicals at atmospheric pressure comprises the steps of:
   applying a high voltage to an atmospheric plasma cell so as to generate a plasma; and
   providing a flow of gas through the plasma to generate the oxidizing plasma radicals.

3. The method of claim 2, further comprising the step of:
   filtering the plasma radicals from the gas and releasing the filtered gas from the sterilization container to the atmosphere.

4. The method of claim 3, further comprising the step of releasing the filtered gas to the atmosphere only once the sterilization container has reached a predetermined pressure level.

5. The method of claim 2, further comprising the steps of:
   powering off the high voltage to the atmospheric plasma cell once the article is sterilized; and
   removing the sterilized article from the sterilization container once the plasma radicals have been filtered from the sterilization container.

6. The method of claim 5, further comprising the step of providing a gas to the sterilization container prior to the removal of the sterilized article.

7. The method of claim 6, wherein the gas is an inert gas.

8. The method of claim 2, wherein the gas comprises dry air with a humidity level below 50%.

9. An apparatus for sterilizing an article, the apparatus comprising:
a sterilization container for receiving an article to be sterilized;
a plasma radical generator for generating oxidizing plasma radicals at atmospheric pressure;
means for providing the oxidizing plasma radicals to the sterilization container; and
means for providing an even distribution of oxidizing plasma radicals within the sterilization container.

10. The apparatus of claim 9, wherein the plasma radical generator comprises:
a high voltage power supply coupled to an atmospheric plasma cell for generating a plasma discharge; and
a gas source for providing a flow of gas to the atmospheric plasma cell.

11. The apparatus of claim 10, further comprising an exhaust system coupled to the sterilization container for filtering the plasma radicals from the gas prior to releasing the gas from the sterilization container to the atmosphere.

12. The apparatus of claim 11, further comprising means for releasing the filtered gas to the atmosphere only once the sterilization container has reached a predetermined pressure level.

13. The apparatus of claim 12, wherein the sterilization container includes a gas outlet and wherein the means for releasing the filtered gas to the atmosphere only once the sterilization container has reached a predetermined pressure level comprises a back pressure valve provided on the gas outlet of the sterilization container.

14. The apparatus of claim 10, wherein the atmospheric plasma cell is separate to the sterilization container and the means for providing the oxidizing plasma radicals to the sterilization container comprises a gas inlet port located on the sterilization container for connecting the atmospheric plasma cell to the sterilization container.

15. The apparatus of claim 14, further comprising a non return valve located adjacent to the gas inlet port and configured to prevent a back flow of oxidizing plasma radicals to the atmospheric plasma cell.

16. The apparatus of claim 10, wherein the atmospheric plasma cell is located within the sterilization container, and the means for providing the oxidizing plasma radicals to the sterilization container comprises a circulation means located in the sterilization container to circulate the plasma radicals.

17. The apparatus of claim 10, wherein the sterilization container comprises a plastic bag.

18. The apparatus of claim 9, where the means for providing an even distribution of the oxidizing plasma radicals comprises a plurality of pipes coupled to a gas inlet port of the sterilization container, each pipe having a plurality of apertures distributed along its length.

19. The apparatus of claim 9, where the means for providing an even distribution of the oxidizing plasma radicals comprises a custom nozzle coupled to a gas inlet port of the sterilization chamber.

* * * * *